(12) United States Patent
Negi et al.

(10) Patent No.: US 8,633,242 B2
(45) Date of Patent: Jan. 21, 2014

(54) BENZYLIDENE INDANONES AND PROCESSES FOR PREPARATION AND USE THEREOF

(71) Applicant: Council of Scientific and Industrial Research, New Delhi (IN)

(72) Inventors: Arvind Singh Negi, Lucknow (IN); Ayyampudur Palanisamy Prakasham, Lucknow (IN); Ajit Kumar Saxena, Jammu (IN); Suaib Luqman, Lucknow (IN); Debabrata Chanda, Lucknow (IN); Tandeep Kaur, Jammu (IN); Atul Gupta, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 13/623,161

(22) Filed: Sep. 20, 2012

(65) Prior Publication Data

US 2013/0079396 A1    Mar. 28, 2013

(30) Foreign Application Priority Data

Sep. 22, 2011    (IN) .......................... 2769/DEL/2011

(51) Int. Cl.
| | | |
|---|---|---|
| *A61K 31/36* | (2006.01) | |
| *A61K 31/12* | (2006.01) | |
| *C07D 317/54* | (2006.01) | |
| *C07C 49/755* | (2006.01) | |
| *C07C 201/12* | (2006.01) | |
| *C07C 45/72* | (2006.01) | |
| *C07C 205/45* | (2006.01) | |

(52) U.S. Cl.
USPC ........... 514/464; 514/681; 514/677; 549/446; 568/327; 568/306

(58) Field of Classification Search
USPC ........... 514/464, 681, 677; 549/446; 568/327, 568/306
See application file for complete search history.

(56) References Cited

PUBLICATIONS

Prakasham et al., Synthesis and anticancer activity of 2-benzylidene indanones through inhibiting tubulin polymerization, 2012, Bioorganic & Medicinal Chemistry, 20, 3049-3057.*
Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*

* cited by examiner

*Primary Examiner* — Kristin Vajda
(74) *Attorney, Agent, or Firm* — Drinker Biddle & Reath LLP

(57) ABSTRACT

The present invention relates to benzylidene indanones of general formula 1. The compounds exhibited tubulin polymerisation inhibition. A series of compounds 2-benzylidene 3-(3,4,5-trimethoxyphenyl) indanones having general formula 1 were synthesized from gallic acid through a chemical process. 2-(3,4-Methylenedioxybenzylidine), 3-(3,4,5-trimethoxyphenyl), 4,5,6-trimethoxyindanone (8), a representative compound of this series possessing the molecular formula $C_{29}H_{28}O_9$, was synthesized from gallic acid and exhibits potent anticancer activity. Compound 8 was evaluated for acute oral activity in Swiss albino mice and found to be safe up to 300 mg/kg body weight. The anticancer activity of the compounds has been determined, in order to obtain new potent and cost effective molecules using an in vitro cytotoxicity assay.

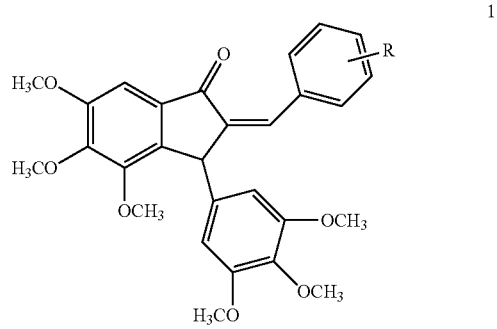

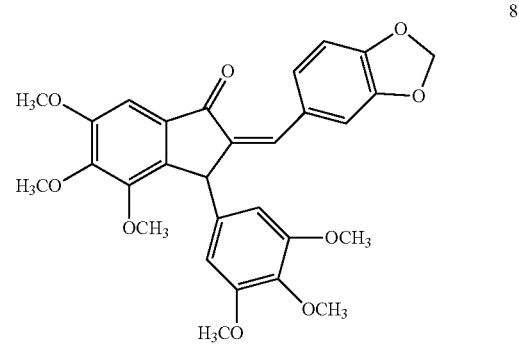

9 Claims, 2 Drawing Sheets

BENZYLIDENE INDANONES AND PROCESSES FOR PREPARATION AND USE THEREOF

FIELD OF THE INVENTION

The present invention relates to benzylidene indanones. This invention provides a new series of gallic acid based 2-benzylidene indanones possessing potent anticancer activity against several human cancer cell lines. More particularly, the invention relates to the potent anticancer and tubulin polymerisation inhibition activity of new benzylidene indanones of general formula (1) synthesized from gallic acid. This invention also provides a new process for the preparation of the said molecules and testing these for in vitro cytotoxic activity against various human cancer cell fines using Sulphorhodamine B Assay.

Compound 8 was evaluated for acute oral activity in Swiss albino mice and it was found to be safe up to 300 mg/kg body weight.

BACKGROUND AND PRIOR ART

Cancer, the uncontrolled growth of cells is a leading cause of death worldwide and accounted for 7.6 million deaths (around 13% of all total deaths) in 2008 [WHO Factsheet No 297, February 2011]. Globally, breast cancer is the leading cause of cancer death among women. More than 70% of all cancer deaths occurred in low- and middle-income countries. Deaths from cancer worldwide are projected to continue rising, with an estimated over 11 million deaths in 2030. [Cancer-WHO Factsheet No 297, February 2011].

Several approaches have been developed for clinical use in the last 25 years. For cancer-chemotherapy many antitumour drugs have been developed for clinical use. Efforts have been done to combat with cancer all over the world and several anticancer molecules have come as a result. These molecules are from both natural products & synthetic and the analogues of these natural products. The natural leads are such as vincristine, vinblastine, taxol (paclitaxel), camptothecin, podophyllotoxin, combretastatins etc. Some of these are being used as a drug for cancer treatment. Synthetic analogues of these natural products like taxotere, topotecan, irinotecan, etoposide, teniposide etc have also been developed as cancer drugs. But, current chemotherapeutic antitumour drugs suffer two major drawbacks, adverse effects and drug resistance. Adverse effects associated with conventional autitumour drugs are due to their indiscriminate cytotoxic effect on normal cells. In the treatment of solid tumours, the conventional approaches have met with only limited success, and cancer still remains as one of the leading cause of human mortality. Drug resistance is another problem associated with these drugs due to elongated treatment. In drug resistance, the use of combination therapy, which is the administration of several drugs with different and complimentary mechanisms of action, is regarded as the more effective approach. But, the side effects are also additive due to multiple therapies. Therefore, the object of today is to overcome the shortcomings of the present cancer chemotherapy with an antitumour drug with a new mechanism of action, capable of discriminating tumour cells from normal proliferate cells and exhibiting selectivity against cancer.

Gallic acid (2), is a plant phenolic acid present as hydrolysable tannins in almost all woody perennials. Gallic acid has been a building block of choice for several synthetic bioactive lead molecules. A number of derivatives possessing gallic acid moiety are reported to possess various pharmaceutical activities like anticancer [Pettit et al., J. Nat. Prod, 2000, 63(7), 969-974.;], antimalarial [Griffith et al., Bioorg. Med. Chem. Lett. 2002, 12(4), 539-542], antioxidants [Masuda et al, J. Nat. Prod. 1998, 61, 609-613], HIV-1 integrase [Carlson et al., J. Med. Chem. 2000, 43(11), 2100-2114], HIV-1 RT [Tillekeratne et al., Bioorg. Med. Chem. Lett. 2001, 11, 2763-2767; Tillekeratne et al., Bioorg. Med. Chem. Lett. 2002, 12(4), 525-528] etc.

Indanones are bioactive molecules. These compounds have mainly been explored as anticancer agents [Lawrence et al., Tetrahedron Lett. 2006, 47, 1637]. Indanocine and its analogues are being developed to combat drug resistance malignancies [Leoni et al., J. Natl. Cancer Inst. 2000, 92, 217.] [Jason G. Taylor et al, Facile synthesis of symmetrical 3,3-diarylacrylates by a Heck-Matsuda reaction: an expedient route to biologically active indanones, Tetra. Lett 2011, onlin-released]

Bansal et al. [PCT Int. Appl. (2007), WO 2007031833 A2 20070322] prepared some indan 1-one derivatives as aromatase inhibitors. Aromatase inhibitors are used for breast cancer and ovarian cancer. Aromatase inhibitors block biosynthesis of estrogens. Brendel K. et. al. [Hung. Pat. Appl. (2000), HU 9903620 A2 20000228] developed a pharmaceutical composition of some benzylidene indenyl formamides for the use as anticancer drugs. Kamimura D. et. al. [Jpn. Kokai Tokkyo Koho (19996), JP 08198798 A 19960806] isolated an antitumour indanone derivative i.e. 5-bromo-4,7-dihydroxyindan-1-one from animal sponge inhibiting proliferation of mouse lymphatic leukemia cells.

The applicants have been working on development of anticancer agents. We designed and modified gallic acid to various aryl naphthofurans [Srivastava et al., Bioorg. Med. Chem. Lett., 2006, 16: 911-9141], naphthophenone fatty acid amides [Srivastava et. al., Bioorg. Med. Chem. Lett., 2006, 16: 4603-4608], chalcones [Steroids, 2007, 72: 892-900] and indanones [Bioorg. Med. Chem. Lett., 2008, 18: 3914-3918] as possible anticancer agents. The applicants have been working on structural modifications of gallic acid to several anticancer agents [Srivastava et al, Bioorg. Med. Chem. Lett., 2006, 16: 911-914; Srivastava et al., Bioorg. Med. Chem. Lett., 2006, 16: 4603-4608; Saxena et al., Bioorg. Med. Chem. Lett., 2008, 18: 3914-3918]. In the present invention gallic acid have been modified to few 2-benzylidene 3-(3,4,5-trimethoxyphenyl) indanones as anticancer agents. Some of the analogues have exhibited potent anticancer activity [Skehan et. al., J. Natl. Cancer Inst., 1990, 82: 1107]. Some of the analogues showed strong inhibition of tubulin polymerisation [Shelanski et. al., Proceedings of Natl. Acad. Sci., 1973, 70: 765-768; Lee J C, Biochem., 1977, 16: 1754-62].

The present series was designed and synthesized as 2-benzylidene analogues of gallic acid based indanones. There are six synthetic steps involved in the preparation of these compounds. We have already reported up to first five steps [Saxena et al., Bioorg. Med. Chem. Lett., 2008, 18: 3914-3918]. All the reported molecules (8-22) of final step are novel. The synthetic steps are simple and straight forward. In few steps purification of compounds is required. These benzylidene indanones exhibited good anticancer activity against various human cancer cell lines i.e. A549 (Lung). PC-3 (Prostate), HCT (Colon), THP-1 (Leukemia), HeLa (Cervix), MCF-7 (Hormone dependent breast cancer), and DU-145 (prostate). These analogues also inhibited tubulin polymerisation in invitro assay.

OBJECTS OF THE INVENTION

The main object of this invention is to provide benzylidene indanones of general formula 1.

Another object of the invention is to provide the new anticancer molecules i.e. 2-benzylidene 3-(3,4,5-trimethoxyphenyl) indanones.

It is also an object of the invention to provide a process of preparation of these biologically active molecules represented by general formula 1 in good yields, from readily available starting material gallic acid (2).

Yet another object of the invention is to provide an effective amount of these new molecules as anticancer agents.

SUMMARY OF THE INVENTION

Accordingly the present invention provides a compound of general formula 1,

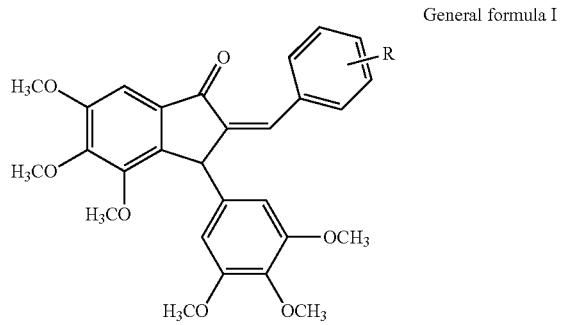

General formula I wherein R is selected from a group consisting of H., 3,4-methylenedioxy, 3,4,5-trimethoxy, 4-methoxy, 4-nitro, 3-nitro, 3,4-dimethoxy, 2,3,4-trimethoxy, 2,4,5-trimethoxy, 2,3-methylenedioxy, 4-fluoro, 2-methoxy, 4-trifluoromethyl, 2,4-dimethoxy, 4-benzyloxy.

In an embodiment of the invention wherein the representative compounds comprising:
(i) 2-(3,4-Methylenedioxybenzylidine), 3-(3,4,5-trimethoxyphenyl), 4,5,6-trimethoxyindanone (8);
(ii) 2-(3",4",5"-trimethoxybenzylidene), 3-(3',4',5'-trimethoxyphenyl)-4,5,6-trimethoxy indan-1-one (9);
(iii) 2-(4"-methoxybenzylidene),3(3',4',5'-trimethoxyphenyl)-4,5,6-trimethoxy indan-1-one (10);
(iv) 2-(4"-nitrobenzlidene),3-(3',4',5'-trimethoxyphenyl)-4,5,6-trimethoxy indan-1-one (11);
(v) 2-(3"-nitrobenzylidene),3-(3',4',5'-trimethoxyphenyl)-4,5,6-trimethoxy indan-1-one (12)
(vi) 2-(3",4"-dimethoxybenzylidene), 3-(3',4',5'-trimethoxyphenyl)-4,5,6-trimethoxy indan-1-one (13);
(vii) 2-benzylidene, 3-(3',4',5'-trimethoxyphenyl)-4,5,6-trimethoxy indan-1-one (14);
(viii) 2-(2",3",4"-trimethoxybenzylidene), 3-(3',4',5'-trimethoxyphenyl)-4,5,6-trimethoxy, indan-1-one (15);
(ix) 2-(2",4",5"-trimethoxybenzylidene), 3-(3',4',5'-trimethoxyphenyl)-4,5,6-trimethoxy indan-1-one (16);
(x) 2-(2",3"-methylenedioxybenzlidene), 3-(3',4',5'-trimethoxyphenyl)-4,5,6-trimethoxy indan-1-one (17);
(xi) 2-(4"-fluorobenzylidene), 3-(3',4',5'-trimethoxyphenyl)-4,5,6-trimethoxy indan-1-one (18);
(xii) 2-(2"-methoxybenzylidene), 3-(3',4',5'-trimethoxyphenyl)-4,5,6-trimethoxy indan-1-one (19);
(xiii) 2-(4"-trifluoromethylbenzylidene), 3-(3',4',5'-trimethoxyphenyl)-4,5,6-trimethoxy indan-1-one (20);
(xiv) 2-(2",4"-dimethoxybenzylidene), 3-(3',4',5'-trimethoxyphenyl)-4,5,6-trimethoxy indan-1-one (21);
(xv) 2-(4"-benzyloxybenzylidene), 3-(3',4',5'-trimethoxyphenyl)-4,5,6-trimethoxy indan-1-one (22).

In another embodiment of the invention wherein the structural formula of the compounds comprising:

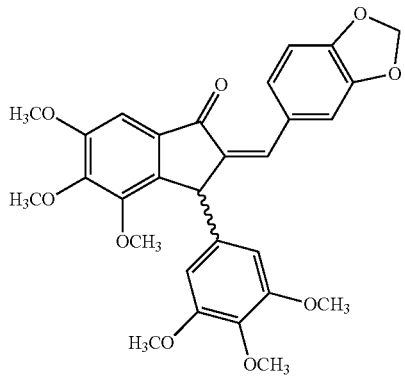

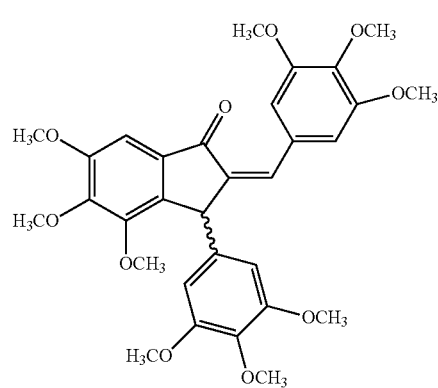

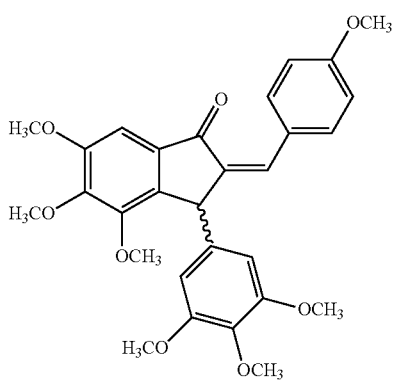

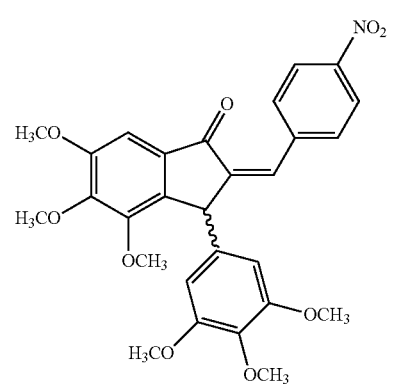

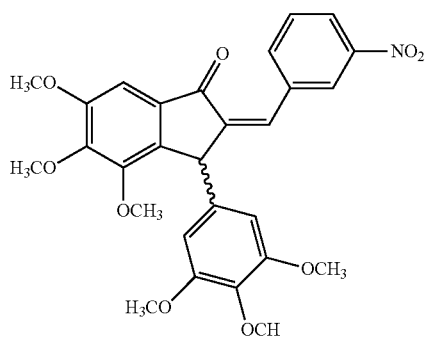
12
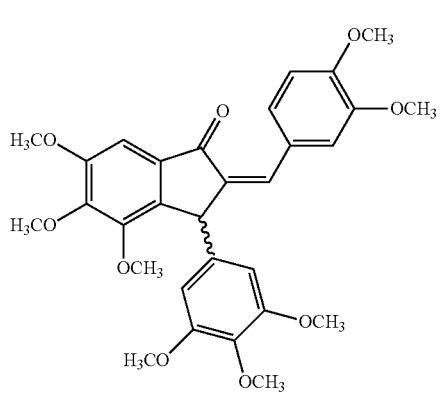
13
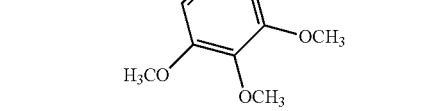
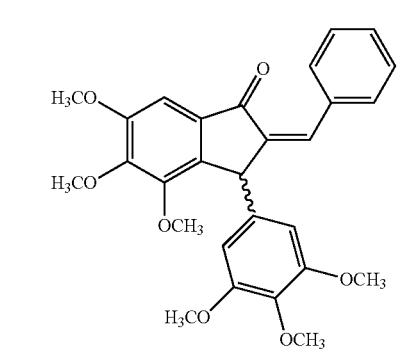
14
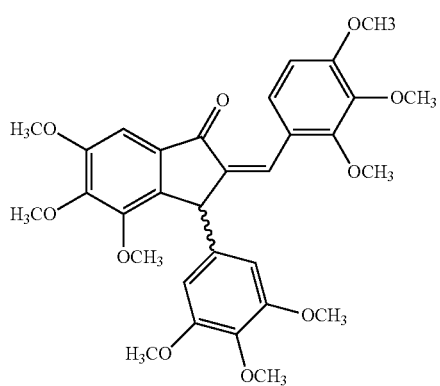
15
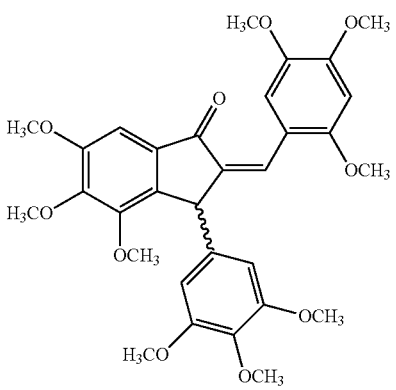
16
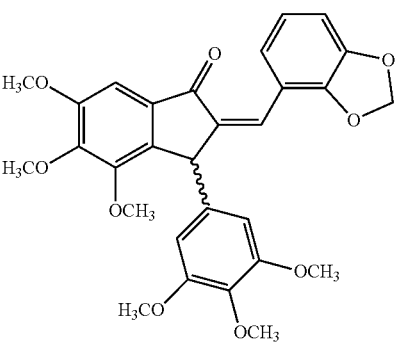
17
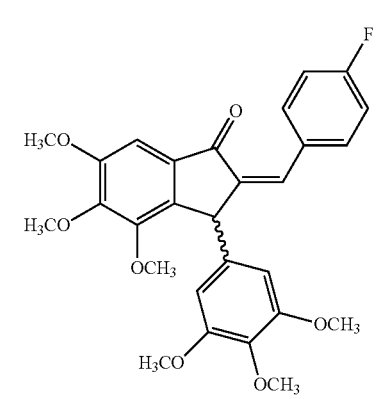
18
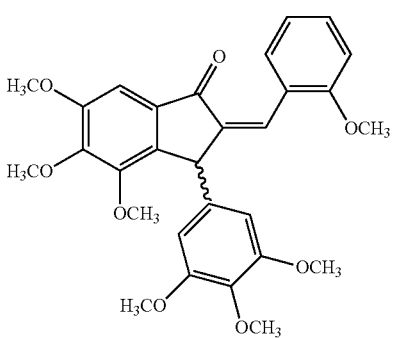
19

-continued

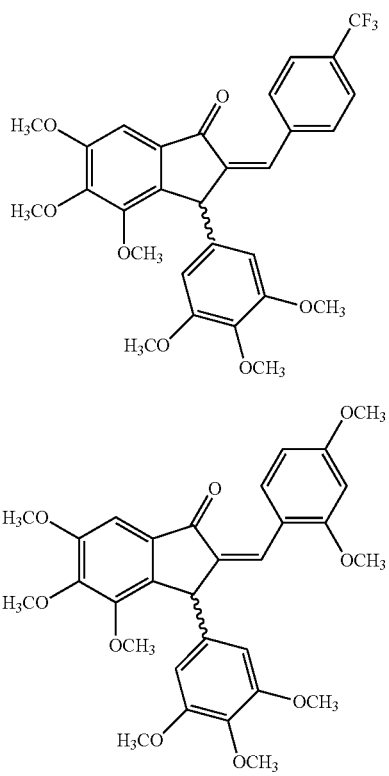

20

21

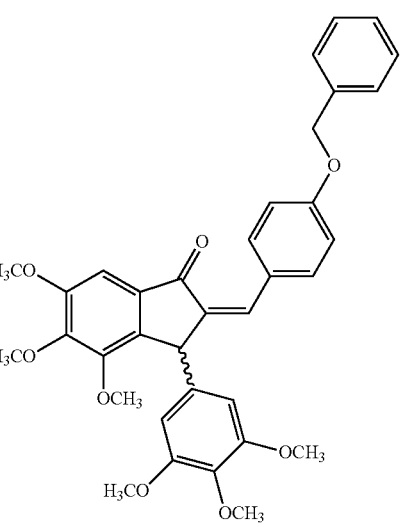

22

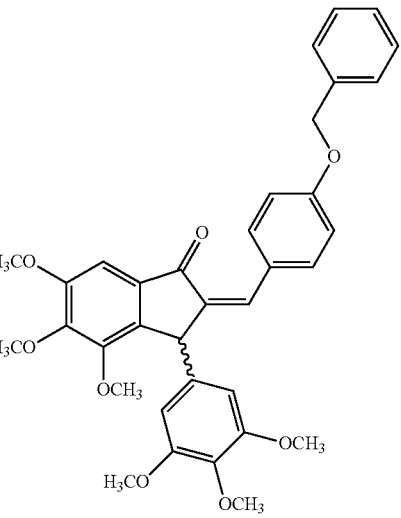

In yet another embodiment of the invention wherein the compounds have tubulin polymerisation inhibition activity.

In still another embodiment of the invention wherein the compounds are useful as anticancer agent.

In a further embodiment of the invention wherein the compound represented by formula 8, exhibits cytotoxicity against various human cancer cell lines, $IC_{50}$ ranging from 0.01 μM (10 nM) to 11 μM.

In an embodiment of the invention wherein the compound represented by formula 8, exhibits better activity against MCF-7 (breast) and HCT (Colon) cancer cell lines.

Accordingly the present invention also provides a process for preparing the compound of general formula 1, wherein the process steps comprising;

(a) reacting 4,5,6-trimethoxy-3-(3,4,5-trimethoxyphenyl)-indan-1-one (7) with an aromatic aldehyde in alkaline solution at a temperature ranging between 20 to 35° C. to for a period ranging between 1 to 4 hr, (b) diluting the reaction mixture with water and acidified with HCl followed by extraction with a water immiscible solvent and evaporating to obtain a residue, and (c) purifying the residue of step (b) by chromatographic methods to give compound of formula 1.

In an embodiment of the invention wherein the aromatic aldehyde used may be selected from a group consisting of 3,4-methylenedioxybenzaldehyde; 3,4,5-trimethoxybenzaldehyde; 4-methoxybenzaldehyde; 4nitrobenzaldehyde; 3-nitrobenzaldehyde; 3,4,-dimethoxybenzaldehyde; benzaldehyde; 2,3,4-trimethoxybenzaldehyde; 2,4,5-trimethoxybenzaldehyde; 2,3-methylenedioxybenzaldehyde; 4-fluorobenzaldehyde; 2-methoxybenzaldehyde; 4-trifluoromethylbenzaldehyde; 2,4,-dimethoxybenzaldehyde; and 4-benzyloxybenzaldehyde.

In another embodiment of the invention wherein the alkali used in alkaline solution may be selected form a group consisting of KOH, sodium hydroxide, lithium hydroxide, potassium carbonate, sodium carbonate.

In yet another embodiment of the invention wherein the alkaline solution used is ranging between 3% to 10%).

In still another embodiment of the invention wherein the alcohol used in aqueous alcohol may be selected form a group consisting of methanol, ethanol in 50-100% concentration in water.

DETAILED DESCRIPTION OF THE INVENTION

Figure 1A:
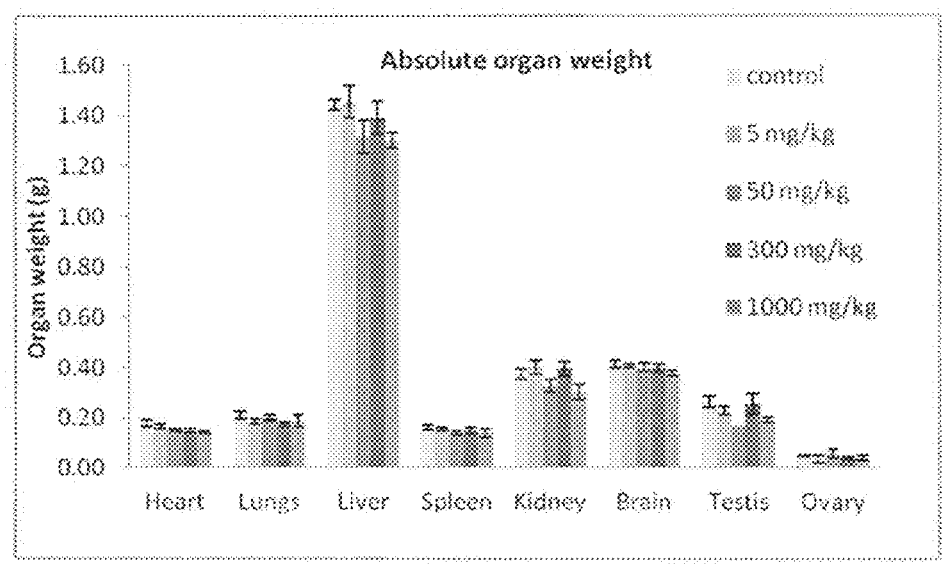
FIG. 1. Effect of compound 8 as a single acute oral dose at 5, 50, 300 and 1000 mg/kg on absolute (FIG. 1A) and relative (FIG. 1B) organ weight in Swiss albino mice. (n=6, Non significant changes were found compared to control).

The present invention provides a new molecule i.e. 2-(3,4-methylenedioxybenzylidine), 3-(3,4,5-trimethoxyphenyl), 4,5,6-trimethoxyindanone represented by structural formula (8) as shown herein;

8

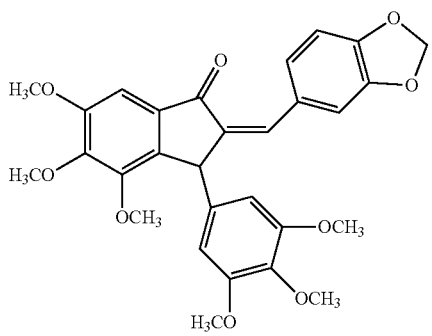

The compound exhibits anticancer and tubulin polymerisation inhibition activity.

Synthesis: The process for preparation of this novel compound comprises six synthetic steps of; a) Methylation of gallic acid with a methlating agent to get a trimethoxy methyl benzoate (3); (b) Reduction of ester to trimethoxybenzyl alcohol (4) with a suitable reducing agent; (c) Oxidation of benzyl alcohol to trimethoxybenzaldehyde (5) with a suitable oxidizing agent; (d) Condensation of trimethoxybenzaldehyde with a trimethoxyacetophenone in an alkaline solution to get a chalcone unit (6); (e) Conversion of chalcone unit to indanone moiety (7) by treating with a reagent; (f) Condensation of the indanone unit with a suitable aromatic aldehyde in alkaline solution to obtain the final compound 8.

[Synthesis up to step e our previous publication—Saxena, H O; Faridi, U; Srivastava, S.; Kumar, J K; Darokar, M P; Luqman, S.; Chanotiya, C S; Krishna, V.; Negi, A S, *Bioorg. Med. Chem. Lett.*, 2008, 18: 3914-3918.]

Similarly, other members of this series have been synthesized by using different aldehydes in step (f) under similar reaction conditions to get benzylidene indanones having structural formula 9-22. 3,4,5-trimethoxybenzaldehyde yields 9 [3-(3',4',5'-trimethoxyphenyl)-4,5,6-trimethoxy, 2-(3",4",5"-trimethoxybenzylidene)-indan-1-one]; 4-methoxybenzaldehyde yields 10 [3-(3',4',5'-trimethoxyphenyl)-4,5,6-trimethoxy,2-(4"-methoxybenzylidene)-indan-1-one]; 4-nitrobenzaldehyde yields 11[3-(3',4',5'-trimethoxyphenyl)-4,5,6-trimethoxy,2-(4"-nitrobenzylidene)-indan-1-one]; 3-nitrobenzaldebyde yields 12 [3-(3',4',5'-trimethoxyphenyl)-4,5,6-trimethoxy,2-(3"-nitrobenzylidene)-indan-1-one]; 3,4-dimethoxybenzaldehyde yields 13 [3-(3',4',5'-trimethoxyphenyl)-4,5,6-trimethoxy, 2-(3",4"-dimethoxybenylidene)-indan-1-one]; benzaldehyde yields 14 [3-(3',4',5'-trimethoxyphenyl)-4,5,6-trimethoxy, 2-benzylidene-indan-1-one]; 2,3,4-trimethoxybenzaldehyde yields 15 [3-(3',4',5'-trimethoxyphenyl)-4,5,6-trimethoxy, 2-(2",3",4"-trimethoxybenzylidene)-indan-1-one]; 2,4,5-trimethoxybenzaldehyde yields 16 [3-(3',4',5'-trimethoxyphenyl)-4,5,6-trimethoxy,2-(2",4",5"-trimethoxybenzylidene)-indan-1-one]; 2,3-methylenedioxybenzaldehyde yields 17 [3-(3',4',5'-trimethoxyphenyl)-4,5,6-trimethoxy, 2-(2",3"-methylenedioxybenzylidene)-indan-1-one]; 4-fluorobenzaldehyde yields 18 [3-(3',4',5'-trimethoxyphenyl)-4,5,6-trimethoxy,2-(4"-fluorobenzylidene)-indan-1-one]; 2-methoxybenzaldehyde yields 19 [3-(3',4',5'-trimethoxyphenyl)-4,5,6-trimethoxy, 2-(2"-methoxybenzylidene)-indan-1-one]; 4-trifluoromethylbenzaldehyde yields 20[3-(3',4',5'-trimethoxyphenyl)-4,5,6-trimethoxy,2-(4"-trifluoromethylbenzylidene)-indan-1-one]; 2,4,-dimethoxybenzaldehyde yields 21 [3-(3',4',5'-trimethoxyphenyl)-4,5,6-trimethoxy, 2-(2",4"-dimethoxybenzylidene)-indan-1-one] and 4-benzyloxybenzaldehyde yields 22 [3-(3',4',5'-trimethoxyphenyl)-4,5,6-trimethoxy, 2-(4"-benzyloxybenzylidene)-indan-1-one]. The details of examples 8-22 is given in the Table 1 and 2 below;

Table 1: All the compounds 8-22 are prepared from compound no 7 using the following reaction conditions:

[The molar ratio; compound 7: aldehyde=1:1.2], but if this ratio varies still reaction will go.]

[Reaction goes at room temperature 20-35° C., preferably at 30° C.]

| Compd. no. | Aldehyde | solvent | Temperature | Time (hr) |
|---|---|---|---|---|
| 8 | 3,4-methylenedioxybenzaldehyde | methanol | Ambient Temp. (20-35° C.) | 2 |
| 9 | 3,4,5-trimethoxybenzaldehyde | methanol | Ambient Temp. (20-35° C.) | 3 |
| 10 | 4-methoxybenzaldehyde | methanol | Ambient Temp. (20-35° C.) | 2 |
| 11 | 4-nitrobenzaldehyde | methanol | Ambient Temp. (20-35° C.) | 3 |
| 12 | 3-nitrobenzaldehyde | methanol. | Ambient Temp. (20-35° C.) | 2 |
| 13 | 3,4-dimethoxybenzaldehyde | methanol | Ambient Temp. (20-35° C.) | 1 |
| 14 | benzaldehyde | methanol | Ambient Temp. (20-35° C.) | 2 |
| 15 | 2,3,4-trimethoxybenzaldehyde | methanol | Ambient Temp. (20-35° C.) | 2 |
| 16 | 2,4,5-trimethoxybenzaldehyde | methanol | Ambient Temp. (20-35° C.) | 2 |
| 17 | 2,3-methylenedioxybenzaldehyde | methanol | Ambient Temp. (20-35° C.) | 2 |
| 18 | 4-fluorobenzaldehyde | methanol | Ambient Temp. (20-35° C.) | 1 |
| 19 | 2-methoxybenzaldehyde | methanol | Ambient Temp. (20-35° C.) | 2 |
| 20 | 4-trifluoromethylbenzaldehyde | methanol | Ambient Temp. (20-35° C.) | 3 |
| 21 | 2,4-dimethoxybenzaldehyde | methanol | Ambient Temp. (20-35° C.) | 3 |
| 22 | 4-benzyloxybenzaldehyde | methanol | Ambient Temp. (20-35° C.) | 3 |

TABLE 2

Physical data of examples 8-22

| Compd. no. | Yield (%) | m.p. °C. | Spectral data |
|---|---|---|---|
| 8 | 77 | 199-201 | $^1$HNMR (CDCl$_3$): δ3.41 (s, 13H, OCH$_3$), 3.76 (s, 9H, 3xOCH$_3$), 3.93 (d, 6H, 2x OCH$_3$), 5.26 (s, 1H, 3-CH), 5.95 (bs, 2H, O—CH$_2$—O), 6.49 (s, 2H, 2xCH aromatic), 6.73 (d, 1H, CH aromatic), 7.1 (m, 2H, 2xCH aromatic), 7.23 (s, 1H CH aromatic), 7.61 (s, 1H, CH benzylidene); in $^{13}$C NMR (CDCl$_3$): δ46.7, 56.58, 56.58, 56.58, 56.66, 60.61, 61.26, 61.26, 101.78, 101.90, 106.49, 108.70 ,110.70, 128.00, 128.95, 132.53, 134.87, 137.20, 137.20, 138.17, 141.22, 148.23, 148.96, 149.37, 150.34, 153.43, 153.43, 155.28, 194.10, ESI-MS (MeOH): 521 [M + H]$^+$, 543 [M + Na]$^+$, 559 [M + K]$^+$. |
| 9 | 78 | 118-20 | $^1$H NMR (CDCl$_3$, 300 MHz): δ 3.51 (s, 3H, OCH$_3$), 3.66 (s, 3H, OCH$_3$), 3.72 (s, 6H, 2xOCH$_3$), 3.74 (s, 6H, 2xOCH$_3$), 3.79 (s, 3H, OCH$_3$), 3.82 (s, 3H, OCH$_3$), 3.83 (s, 3H, OCH$_3$), 5.19 (s, 1H, 3-CH), 6.49 (s, 2H, 2' & 6'-CH of 3-phenyl), 6.61 (s, 2H, 2" & 6"-CH), 7.13 (s, 1H, 7-CH), 7.55 (s, 1H, benzylidene-CH), $^{13}$C NMR (CDCl$_3$, 75 MHz); δ 46.70, 60.42, 60.42, 60.42, 60.66, 60.66, 60.66, 61.15, 61.18, 61.18, 101.78, 105.84, 106.55, 106.55, 109.30, 109.30, 130.11, 132.13, |

TABLE 2-continued

Physical data of examples 8-22

| Compd. no. | Yield (%) | m.p. °C. | Spectral data |
|---|---|---|---|
| | | | 135.30, 136.83, 136.83, 137.26, 140.11, 140.34, 150.32, 153.39, 153.46, 153.46, 153.46, 155.27, 193.93, ESIMS (MeOH): 567 [M + H]⁺, 589 [M + Na]⁺, 605 [M + K]⁺. |
| 10 | 81 | 188-90 | ¹H NMR (CDCl₃, 300 MHz): δ 3.49 (s, 3H, OCH₃), 3.76 (s, 9H, 3xOCH₃), 3.82 (s, 3H, OCH₃), 3.91 (s, 3H, OCH₃), 3.94 (s, 3H, OCH₃), 5.29 (s, 1H, 3-CH), 6.51 (s, 2H, 2' & 6'-CH of 3-phenyl), 6.79-6.82 (d, 2H, 2" & 6"-CH, J = 8.7 Hz), 7.24 (s, 1H, 7-CH), 7.49-7.52 (d, 2H, 3" & 5"-CH), 7.68 (s, 1H, benzylidene-CH), ¹³C NMR (CDCl₃, 75 MHz): δ 46.20, 55.25, 56.14, 56.14, 56.21, 56.21, 60.20, 60.83, 101.35, 105.96, 105.96, 113.86, 113.86, 126.91, 132.16, 133.17, 133.17, 134.44, 136.72, 136.84, 137.21, 140.74, 148.41, 149.91, 152.93, 152.93, 154.78, 160.76, 193.79, ESIMS (MeOH): 507 [M + H]⁺, 529 [M + Na]⁺, 545 [M + K]⁺ |
| 11 | 79 | 190-92 | ¹H NMR (CDCl₃, 300 MHz): δ 3.44 (s, 3H, OCH₃), 3.71 (s, 9H, 3xOCH₃), 3.92 (s, 3H, OCH₃), 3.95 (s, 3H, OCH₃), 5.27 (s, 1H, 3-CH), 6.37 (s, 2H, 2' & 6'-CH of 3-Phenyl), 7.22 (s, 1H, 7-CH), 7.57-7.60 (d, 2H, 2" & 6"-CH), 7.67 (s, 1H, benzylidene-CH), 8.08-8.11 (d, 2H, 3" & 5"-CH), ¹³C NMR (CDCl₃, 75 MHz): δ 46.50, 56.63, 56.63, 56.71, 60.69, 61.29, 61.36, 101.89, 106.35, 106.35, 123.79, 123.79, 131.65, 131.65, 131.78, 131.98, 136.80, 137.47, 141.26, 141.35, 143.96, 147.97, 149.71, 150.35, 153.57, 153.57, 155.61, 193.41, ESIMS (MeOH): 544 [M + Na]⁺, 560 [M + K]⁺ negative mode: 520 [M − H]⁺. |
| 12 | 77 | 215-17 | ¹H NMR (CDCl₃, 300 MHz): δ 3.43 (s, 3H, OCH₃), 3.76 (s, 6H, 2xOCH₃), 3.93 (s, 3H, OCH₃), 3.95 (s, 3H, OCH₃), 5.38 (s, 1H, 3-CH), 6.48 (s, 2H, 2' & 6'-CH), 7.10-7.18 (m, 1H, 5"-CH), 7.26 (s, 1H, 7-CH), 7.45-7.50 (d, 1H, 6"-CH), 7.69 (s, 1H, 2"-CH of benzylidene ring), 8.10-8.13 (d, 1H, 4"-CH of benzylidene ring), 8.46 (s, 1H, benzylidene-CH), ¹³C NMR (CDCl₃, 75 MHz): δ 46.24, 56.05, 56.05, 56.29, 60.24, 60.79, 60.92, 101.44, 105.89, 105.89, 123.75, 124.51, 127.62, 128.08, 129.36, 131.17, 131.52, 135.80, 135.80, 136.88, 137.43, 141.16, 142.51, 148.14, 149.27, 153.09, 155.15, 193.31, ESIMS (MeOH): 521 [M]⁺, 544 [M + Na]⁺. |
| 13 | 85 | 179-80 | ¹H NMR (CDCl₃, 300 MHz): δ 3.56 (s, 3H, OCH₃), 3.73 (s, 6H, 2xOCH₃), 3.75 (s, 9H, 3xOCH₃), 3.86 (s, 3H, OCH₃), 3.90 (s, 3H, OCH₃), 5.28 (s, 1H, 3-CH), 6.39 (s, 2H, 2' & 6'-CH of 3-phenyl), 6.79-6.81 (d, 1H, 5-CH, J = 8.1 Hz), 6.97 (s, 1H, 2-CH), 7.15-7.18 (d, 1H, 6-CH, J = 8.4 Hz), 7.22 (s, 1H, 7-CH), 7.68 (s, 1H, benzylidene-CH), ¹³C NMR (CDCl₃, 75 MHz): δ46.83, 56.31, 56.52, 56.56, 56.56, 56.68, 60.75, 61.26, 61.30, 101.85, 106.22, 106.22, 111.22, 113.88, 126.94, 127.68, 132.48, 135.44, 137.17, 137.28, 140.91, 140.91, 148.78, 149.22, 150.40, 151.11, 153.49, 153.49, 155.27, 194.20, ESIMS (MeOH): 537 [M + H]⁺, 559 [M + Na]⁺, 575 [M + K]⁺. |
| 14 | 89 | 139-41 | ¹H NMR (CDCl₃, 300 MHz): δ 3.43 (s, 3H, OCH₃), 3.69 (s, 9H, 3xOCH₃), 3.88 (s, 6H, 2xOCH₃), 5.26 (s, 1H, 3-CH), 6.40 (s, 2H, 2' & 6'-CH, aromatic), 7.15 (s, 1H, 7-CH), 7.21 (bs, 3H, Phenyl ring), 7.48 (bs, 2H, Phenyl ring of benzylidene), 7.67 (s, 1H, benzylidene-CH), ³³C NMR (CDCl₃, 75 MHz): δ 46.53, 56.57, 56.67, 56.67, 60.66, 61.26, 61.30, 101.83, 106.39, 106.39, 106.39, 128.70, 128.70, 131.43, 129.83, 131.43, 132.46, 134.79, 135.00, 137.15, 137.33, 140.31, 141.44, 149.17, 150.36, 153.34, 153.34, 155.32, 194.17, ESIMS (MeOH): 477 [M + H]⁺, 499 [M + Na]⁺, 515 [M + K]⁺. |
| 15 | 86 | 163-65 | ¹H NMR (CDCl₃, 300 MHz): δ 3.39 (s, 3H, OCH₃), 3.67 (s, 9H, 3xOCH₃), 3.72 (s, 3H, OCH₃), 3.75 (s, 3H, OCH₃), 3.80 (s, 3H, OCH₃), 3.87 (s, 3H, OCH₃), 3.90 (s, 3H, OCH₃), 5.21 (s, 1H, 3-CH), 6.32 (s, 2H, 2' & 6'-CH, 6.48-6.51 (d, 1H, 5"-CH), 7.10-7.14 (d, 1H, 6"-CH), 7.21 (s, 1H, 7-CH, aromatic), 7.88 (s, 1H, benzylidene-CH), ¹³C NMR (CDCl₃, 75 MHz): δ 46.04, 55.93, 56.05, 56.05, 56.05, 56.19, 60.14, 60.78, 60.78, 61.53, 101.32, 105.79, 105.79, 106.65, 121.72, 125.76, 129.71, 132.49, 136.53, 137.30, 139.43, 140.67, 141.98, 148.45, 149.89, 152.73, 152.73, 153.72, 154.75, 154.97, 193.39, ESIMS (MeOH): 568 [M + 2H]⁺ 589 [M + Na]⁺, 605 [M + K]⁺. |
| 16 | 95 | 203-05 | ¹H NMR (CDCl₃, 300 MHz): δ 3.55 (s, 3H, OCH₃), 3.63 (s, 3H, OCH₃), 3.72 (s, 3H, OCH₃), 3.75 (s, 9H, 3xOCH₃), 3.88 (s, 3H, OCH₃), 3.91 (s, 3H, OCH₃), 3.92 (s, 3H, OCH₃), 5.26 (s, 1H, 3-CH), 6.44 (s, 1H, 3"-CH), 6.54 (s, 2H, 2' & 6'-CH of 3-phenyl ring), 6.93 (s, 1H, 6"-CH), 7.23 (s, 1H, 7-CH), 8.79 (s, 1H, benzylidene-CH), ¹³C NMR (CDCl₃, 75 MHz): δ 46.39, 55.87, 55.87, 55.87, 55.98, 56.20, 56.37, 60.24, 60.73, 60.80, 96.44, 101.37, 105.70, 105.70, 114.28, 115.12, 129.27, 132.32, 136.57, 136.57, 137.13, 140.29, 142.62, 148.10, 149.90, 151.95, 152.90, 152.90, 154.69, 155.14, 196.65, 193.39, ESIMS (MeOH): 567 [M + H]⁺, 589 [M + Na]⁺, 605 [M + K]⁺. |
| 17 | 77 | 180-82 | ¹H NMR (CDCl₃, 300 MHz): δ 3.40 (s, 3H, OCH₃), 3.70 (s, 3H, OCH₃), 3.71 (s, 6H, 2xOCH₃), 3.91 (s, 3H, OCH₃), 3.94 (s, 3H, OCH₃), 5.31 (s, 1H, 3-CH), 5.95 & 6.05 (two distinct singlets, 2H, —O—CH2—O), 6.39 (s, 2H, 2' & 6'-CH, aromatic), 6.65-6.70 (m, 2H, 4" & 6"-CH), 6.81-6.90 (dd, 1H, 5"-CH), 7.23 (s, 1H, 7-CH), 7.71 (s, 1H, benzylidine-CH), ¹³C NMR (CDCl₃, 75 MHz): δ 45.99, 56.03, 56.03, 56.19, 60.13, 60.74, 60.83, 100.98, 101.33, 105.73, 105.73, 109.17, 117.15, 121.07, 122.54, 127.32, 132.22, 136.55, 137.04, 140.79, 141.37, 146.80, 147.26, 148.79, 149.90, 152.70, 152.70, 154.80, 193.15, ESIMS (MeOH): 521[M + H]⁺, 543 [M + Na]⁺. |

TABLE 2-continued

Physical data of examples 8-22

| Compd. no. | Yield (%) | m.p. °C. | Spectral data |
|---|---|---|---|
| 18 | 76 | 156-58 | $^1$H NMR (CDCl$_3$, 300 MHz): δ 3.47 (s, 3H, OCH$_3$), 3.73 (s, 9H, 3xOCH$_3$), 3.93 (s, 6H, 2xOCH$_3$), 5.25 (s, 1H, 3-CH), 6.43 (s, 2H, 2' & 6'-CH of 3-phenyl), 6.93-6.99 (t, 2H, 2" & 6"-CH), 7.27 (s, 1H, 7-CH), 7.46-7.51 (t, 2H, 3" & 5"-CH), 7.65 (s, 1H, benzylidene-CH), $^{13}$C NMR (CDCl$_3$, 75 MHz): δ 46.53, 56.59, 56.59, 56.69, 60.67, 61.29, 61.29, 101.81, 106.30, 106.30, 115.76, 116.05, 130.95, 132.35, 133.39, 133.39, 133.50, 133.75, 137.09, 137.21, 139.83, 141.31, 149.17, 150.37, 153.43, 153.43, 155.36, 194.03, ESIMS (MeOH): 495 [M + H]$^+$, 517 [M + Na]$^+$. |
| 19 | 78 | 191-92 | $^1$H NMR (CDCl$_3$, 300 MHz): δ 3.35 (s, 3H, OCH$_3$), 3.67 (s, 6H, 2xOCH$_3$), 3.69 (s, 3H, OCH$_3$), 3.74 (s, 3H, OCH$_3$), 3.89 (s, 3H, OCH$_3$), 3.93 (s, 3H, OCH$_3$), 5.23 (s, 1H, 3-CH), 6.28 (s, 2H, 2' & 6'-CH of 3-phenyl), 6.74-6.82 (bm, 2H, 4" & 5"-CH), 7.22-7.26 (bm, 2H, 3"-CH & 7-CH), 7.38 (bd, 1H, 6"-CH of benzylidene ring), 7.99 (s, 1H, benzylidene-CH), $^{13}$C NMR (CDCl$_3$, 75 MHz): δ 45.98, 55.34, 56.00, 56.00, 56.19, 60.10, 60.73, 60.81, 101.32, 105.78, 105.78, 110.46, 119.70, 123.76, 130.28, 130.56, 132.51, 136.40, 137.33, 140.53, 140.84, 148.58, 149.93, 152.62, 152.62, 154.75, 157.96, 158.33, 193.45, ESIMS (MeOH): 508 [M + 2H]$^+$, 529 [M + Na]$^+$, 545 [M + K]$^+$. |
| 20 | 70 | 188-90 | $^1$H NMR (CDCl$_3$, 300 MHz): δ 3.45 (s, 3H, OCH$_3$), 3.73 (s, 9H, 3xOCH$_3$), 3.92 (s, 3H, OCH$_3$), 3.95 (s, 3H, OCH$_3$), 5.29 (s, 1H, 3-CH), 6.36 (s, 2H, 2' & 6'-CH), 7.24 (s, 1H, 7-CH), 7.51-7.57 (bs, 4H, 2", 3", 5" & 6"-CH), 7.69 (s, 1H, benzylidene-CH), $^{13}$C NMR (CDCl$_3$, 75 MHz): δ 46.40, 56.57, 56.57, 56.70, 60.68, 61.27, 61.35, 101.84, 106.22, 106.22, 125.51, 125.56, 125.56, 131.15, 132.22, 132.22, 132.22, 132.98, 137.07, 137.29, 138.45, 141.38, 142.68, 149.51, 150.37, 153.46, 153.46, 155.50, 193.72, ESIMS (MeOH): 545 [M + H]$^+$, 567 [M + Na]$^+$. |
| 21 | 87 | 191-92 | $^1$H NMR (CDCl$_3$, 300 MHz): δ 3.42 (s, 3H, OCH$_3$), 3.72 (s, 9H, 3xOCH$_3$), 3.77 (s, 3H, OCH$_3$), 3.80 (s, 3H, OCH$_3$), 3.89 (s, 3H, OCH$_3$), 3.93 (s, 3H, OCH$_3$), 5.22 (s, 1H, 3-CH), 6.31-6.34 (d, 1H, 6"-CH, J = 7.5 Hz), 6.34 (s, 1H, 3"-CH), 6.41 (s, 2H, 2' & 6'-CH of 3-Phenyl ring), 7.23 (s, 1H, 7-CH), 7.39-7.42 (d, 1H, 5"-CH), 8.05 (s, 1H, benzylidene-CH), $^{13}$C NMR (CDCl$_3$, 75 MHz): δ 46.81, 55.79, 55.93, 56.54, 56.54, 56.54, 56.68, 60.62, 61.27, 98.29, 101.79, 104.91, 106.27, 106.27, 116.92, 129.89, 132.48, 133.04, 136.91, 137.77, 138.00, 141.11, 148.70, 150.36, 153.22, 153.22, 155.13, 160.81, 162.82, 194.15, ESIMS (MeOH): 537 [M + H]$^+$ 559 [M + Na]$^+$, 575 [M + K]$^+$. |
| 22 | 80 | 188-90 | $^1$H NMR (CDCl$_3$, 300 MHz): δ 3.48 (s, 3H, OCH$_3$), 3.76 (s, 9H, 3xOCH$_3$), 3.92 (s, 3H, OCH$_3$), 3.96 (s, 3H, OCH$_3$), 5.06 (s, 2H, OCH$_2$, benzyl), 5.29 (s, 1H, 3-CH), 6.50 (s, 2H, 2' & 6'-CH of 3-phenyl), 6.87-6.90 (d, 2H, 2" & 6"-CH, J = 8.4 Hz), 7.24 (s, 1H, 7-CH), 7.39-7.41 (bs, 5H, Phenyl ring), 7.50-7.53 (d, 2H, 3" & 5"-CH, J = 8.1 Hz), 7.69 (s, 1H, benzylidene-CH), $^{13}$C NMR (CDCl$_3$, 75 MHz): δ 46.75, 56.60, 56.60, 56.69, 60.68, 61.30, 61.30, 70.45, 101.80, 106.36, 106.36, 115.16, 115.16, 127.60, 127.88, 127.88, 128.58, 129.07, 129.07, 132.62, 133.67, 133.67, 134.82, 136.77, 137.12, 137.31, 137.78, 141.22, 148.88, 150.37, 153.39, 153.39, 155.24, 160.41, 194.26, ESIMS (MeOH): 583 [M + H]$^+$. |

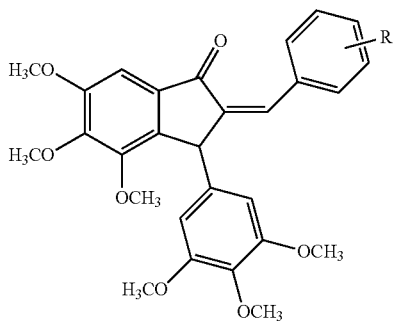

8: R = 3, 4-methylenedioxy; 9: R = 3,4,5-trimethoxy;
10: R = 4-methoxy; 11: R = 4-Nitro; 12: R = 3-nitro;
13: R = 3,4-dimethoxy; 14: R = H; 15: R = 2,3,4-trimethoxy;
16: R = 2,4,5-trimethoxy; 17: R = 2,3-methlenedioxy;
18: R = 4-fluoro; 19: R = 2-methoxy; 20: R = 4-trifluoromethyl;
21: R = 2,4-dimethoxy; 22: R = 4-benzyloxy The methylating agent used in the step (a) may be selected from a group consisting of diazomethane, methyl iodide and dimethyl sulphate. The reducing agent in the step (b) may be selected from the group consisting of sodium borohydride, lithium borohydride, lithium aluminium hydride. The oxidizing agent in step (c) is Pyridinium chlorochromate or chromium trioxide-dipyridine complex. The base used in the step (d) is selected from sodium hydroxide, potassium hydroxide, sodium carbonate, potassium carbonate. The reagent used in the step (e) may be from a group of consisting trifluoroacetic acid, aluminium chloride and methanesulphonic acid. The base used in the step (f) may be selected from a group of bases consisting of potassium hydroxide, potassium carbonate, sodium hydroxide, sodium carbonate.

As mentioned earlier compound 8 exhibits anticancer activity against certain human cancer cell lines especially against MCF-7, HCT, THP-1 and A549 and tubulin polymerisation inhibition. Other compounds of the series having structural formula 9 to 22 also exhibited anticancer activity against various human cancer cell lines and also tubulin polymerisation inhibition.

All these compounds (8-22) have potential use as anticancer agents and also as tubulin polymerisation inhibitors. These would have wide applicability in the pharmaceutical compositions. Without specifying any theory, the applicants state that compound 8 and other compounds 9-22, may be utilised in the pharmaceutical compositions for various cancer treatments or for any other disease related to tubulin disorders.

The invention, its embodiments and applications are described in detail in the examples given below which are provided to illustrate the invention and therefore should not be constructed to limit the scope of this invention.

The schematic diagram for the process of preparation is represented hereunder;

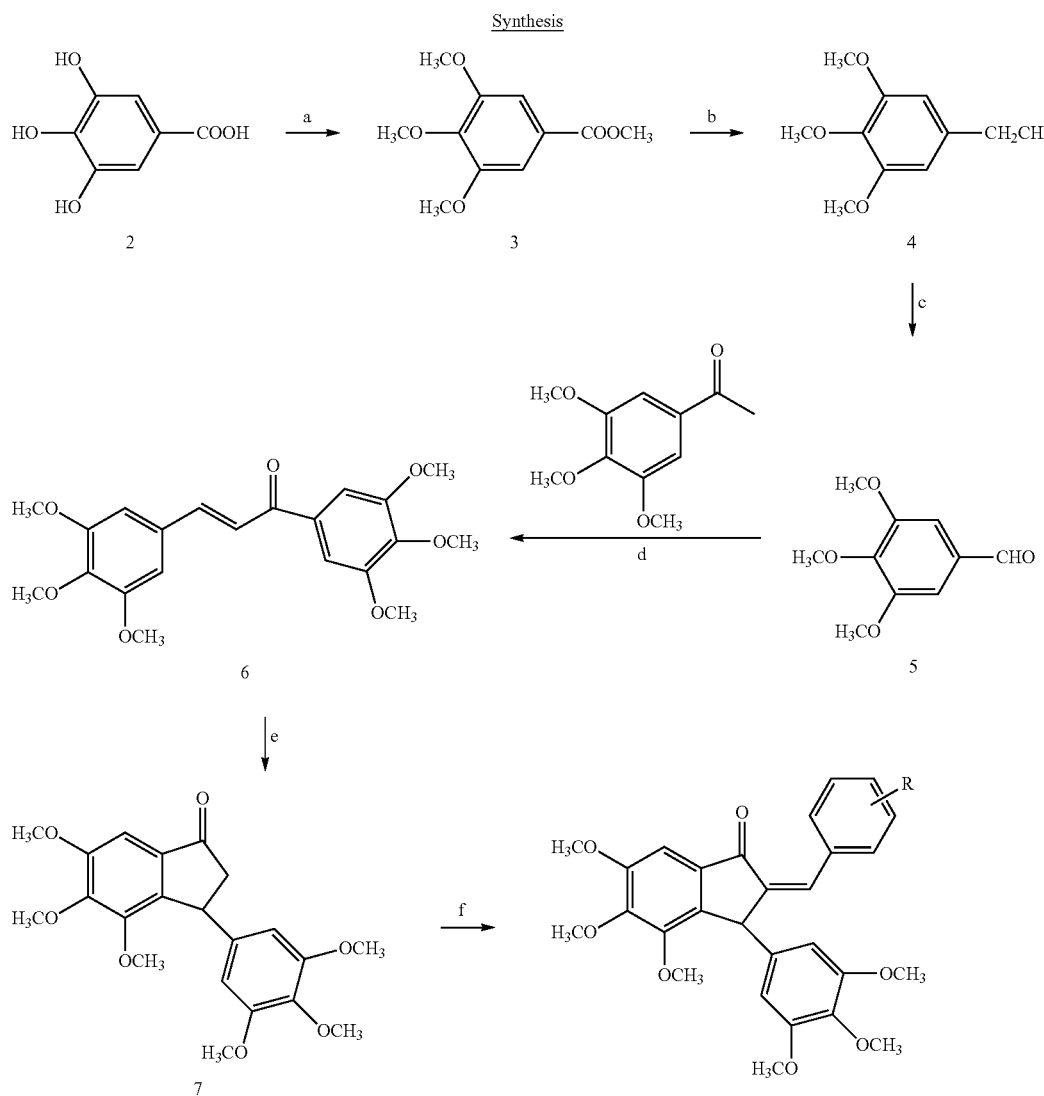

Following examples are given by way of illustration and should not construe to limit the scope of the invention.

EXAMPLE 1

Step 1: Preparation of 3,4,5-trimethoxybenzoic acid methyl ester (Formula 3)

A 50 mL round bottom flask was charged with potassium carbonate (6 g) and dry acetone (15 mL) compound of formula 2 (2 gm) and to it was added methyl iodide (4 mL) and the reaction mixture was refluxed for 5 hours at 60° C. with constant stirring. On completion, the reaction mixture was filtered and washed with acetone and distilled off to get compound of formula 3 (400 mg).

Step 2: Preparation of 3,4,5-trimethoxybenzyl Alcohol (Formula 4)

The compound having formula 3 (400 mg) was stirred in tetrahydrofuran (10 mL) with cooling. To this lithium borohydride (200 mg) was added and further stirred for 3 hours. On completion, the reaction mixture was poured into water, acidified with dil. HCl and extracted with ethyl acetate. The organic layer was washed with water, dried over anhydrous sodium sulphate and evaporated to dryness to get the desired compound of formula 4 (340 g).

Step 3: Preparation of 3,4,5-trimethoxybenzaldehyde (Formula 5)

The compound of formula 4 (340 mg) was taken in dichloromethane (20 mL). To this stirred solution dipyridine-chromium trioxide complex (500 mg) was added and further stirred for 10 hours. On completion the reaction mixture was poured into water and extracted with ethyl acetate. Organic layer was washed with water, dried over anhydrous sodium sulphate and evaporated to dryness. The residue thus obtained was purified through silica gel column and eluted with hexane-ethyl acetate to get the desired compound of formula 5 (190 mg).

Step 4: Preparation of 1,3-bis-(3,4,5-trimethoxyphenyl)-propenone (Chalcone, Formula 6)

To a stirred solution of 3,4,5-trimethoxybenzaldehyde (190 mg, formula 5) in 10% methanolic potassium carbonate (15 mL), 3,4,5-trimethoxyacetophenone (200 mg) was added. It was stirred for 3 hours. On completion, the reaction mixture was diluted with water, acidified with dil. HCl and extracted with ethyl acetate. The organic layer was washed with water, dried over anhydrous sodium sulphate and evaporated to get a residue. The residue was purified through silica gel column to get chalcone of formula 6 (240 mg)

Step 5: Preparation of 4,5,6-trimethoxy-3-(3,4,5-trimethoxyphenyl)-indan-1-one (Formula 7)

1,3-bis-(3,4,5-trimethoxyphenyl)-propenone (chalcone, formula 6, 240 mg) was taken in toluene (10 mL). To reaction mixture methanesulphonic acid (1 mL) was added and refluxed for 4 hours. On completion it was poured into cold water and extracted with ethyl acetate. The organic layer was washed with water, dried over anhydrous sodium sulphate and evaporated to get a residue. The residue was purified through silica gel column to get 4,5,6-trimethoxy-3-(3,4,5-trimethoxyphenyl)-indan-1-one (formula 7, 32 mg).

Step 6: Preparation of 2-(3,4-Methylenedioxybenzylidine), 3-(3,4,5-trimethoxyphenyl), 4,5,6-trimethoxyindanone (Formula 8)

4,5,6-trimethoxy-3-(3,4,5-trimethoxyphenyl)-indan-1-one (formula 7, 32 mg) was taken in 2.5% methanolic potassium hydroxide (15 mL), 3,4-methylenedioxybenzaldehyde (20 mg) was added. It was stirred for 3 hours at room temperature (30° C.). On completion, the reaction mixture was diluted with water, acidified with dil. HCl and extracted with ethyl acetate. The organic layer was washed with water, dried over anhydrous sodium sulphate and evaporated to get a residue. The residue was purified through silica gel column to get 2-(3,4-methylenedioxybenzylidine), 3-(3,4,5-trimethoxyphenyl), 4,5,6-trimethoxyindanone (formula 8, 16 mg).

Spectral details of compound of formula 8:

Compound 8 is a light yellow solid with m.p. 199-201° C. In $^1$HNMR (CDCl$_3$): δ3.41 (s,13H, OCH$_3$), 3.76 (s, 9H, 3×OCH$_3$), 3.93 (d, 6H, 2×OCH$_3$), 5.26 (s, 1H, 3-CH), 5.95 (bs, 2H, O—CH$_2$—O), 6.49 (s, 2H, 2×CH aromatic), 6.73 (d, 1H, CH aromatic), 7.1 (m, 2H, 2×CH aromatic), 7.23 (s, 1H, CH aromatic), 7.61 (s, 1H, CH benzylidene): in $^{13}$C NMR (CDCl$_3$): δ46.7, 56.58, 56.58, 56.58. 56.66, 60.61, 61,26, 61.26, 101.78, 101.90, 106.49, 108.70, 110.70, 128.00, 128.95, 132.53, 134.87, 137.20, 137.20, 138.17, 141.22, 148.23, 148.96, 149.37, 150.34, 153.43, 155.28, 194.10. In electrospray ionization mass (ESI-MS. MeOH) it gives adducts ions at 521 [M+H]$^+$, 543 [M+Na]$^+$, 559 [M+K]$^+$ confirming its molecular formulae as C$_{29}$H$_{28}$O$_9$.

EXAMPLE 2

Step 1: Preparation of 3,4,5-trimethoxybenzoic acid methyl ester (Formula 3)

In a 250 mL round bottom flask 3 g gallic acid was stirred at 0° C. in 20% aqueous potassium hydroxide solution (100 mL). To this dimethyl sulphate (4 mL, 5.34 g) was added dropwise. The reaction mixture was stirred for one hour and the relaxed for 3 hours at 100° C. On completion, the reaction mixture was extracted with ethyl acetate, washed with water, dried over anhydrous sodium sulphate and distilled off to get a residue. It was recrystallised to get compound of formula 3 (1.2 g).

Step 2: Preparation of 3,4,5-trimethoxybenzyl Alcohol (Formula 4)

The compound having formula 3 (1.9 g) was dissolved in tetrahydrofuran (30 mL). To this lithium-aluminium-hydride (1.16 g) was added and refluxed for 1 hour. On completion, the reagent was decomposed by adding ethyl acetate, poured into water, acidified with dil. HCl and extracted with ethyl acetate. The organic layer was washed with water, dried over anhydrous sodium sulphate and evaporated to dryness to get the residue which on purification through silica gel column yielded the desired compound of formula 4 (1.06 g).

Step 3: Preparation of 3,4,5-trimethoxybenzaldehyde (Formula 5)

The compound of formula 4 (1.0 g) was taken in dichloromethane (25 mL). To this stirred solution Pyridinium chlorochromate (1.38 g) was added and further stirred at room temperature for one hour. On completion, the solvent was evaporated and the residue was poured into water and extracted with ethyl acetate. Organic layer was washed with water, dried over anhydrous sodium sulphate and evaporated to dryness. The residue thus obtained was purified through silica gel column to get the desired compound of formula 5 (875 mg).

Step 4: Preparation of 1,3-bis-(3,4,5-trimethoxyphenyl)-propenone (Chalcone, Formula 6)

To a stirred solution of 3,4,5-trimethoxyacetophenone (2.2 g) in aqueous methanolic (1:2) potassium hydroxide (4 g in 70 mL), 3,4,5-trimethoxybenzaldehyde (1.96 g, formula 5) was added. It was stirred at room temperature for 1 hour. The desired chalcone of formula 6 (3.6 g) was obtained after usual workup and suitable column chromatography.

Step 5: Preparation of 4,5,6-trimethoxy-3-(3,4,5-trimethoxyphenyl)-indan-1 one (Formula 7)

1,3-bis-(3,4,5-trimethoxyphenyl)-propenone (chalcone, formula 6, 1 g) was taken in trifluoroacetic acid (1 mL) in a sealed glass-tube and heated at 120° C. for 4 hours. On completion it was poured into cold water and extracted with ethyl acetate. The organic layer was washed with water, dried over anhydrous sodium sulphate and evaporated to get a residue. The residue was purified through silica gel column to get 4,5,6-trimethoxy-3-(3,4,5-trimethoxyphenyl)-indan-1-one (formula 7, 240 mg).

Step 6: Preparation of 2-(3,4-Methylenedioxybenzylidine), 3-(3,4,5-trimethoxyphenyl), 4,5,6-trimethoxyindanone (Formula 8)

4,5,6-trimethoxy-3-(3,4,5-trimethoxyphenyl)-indan-1-one (formula 7, 250 mg) was taken in 2.5% methanolic potassium hydroxide (10 mL). To this stirred solution 3,4-methylenedioxybenzaldehyde (100 mg) was added and further stirred at room temperature at 30° C. for 1 hour. On completion, the reaction mixture was diluted with water, acidified with dil. HCl and extracted with ethyl acetate. The organic layer was washed with water, dried over anhydrous sodium sulphate and evaporated to get a residue. The residue was purified through silica gel column to get 2-benzo[1,3]dioxo-5-ylmethylene-4,5,6-trimethoxy-3-(3,4,5-trimethoxyphenyl)-indan-1-one (formula 8, 258 mg).

EXAMPLE 3

Step 1 to Step 5 Same as in Example 2

Step 6: Preparation of 2-(3,4-methylenedioxybenzlidine), 3-(3,4,5-trimethoxyphenyl), 4,5,6-trimethoxyindanone (Formula 8)

4,5,6-trimethoxy-3-(3,4,5-trimethoxyphenyl)-indan-1-one (formula 7, 250 mg) was taken in 2.5% methanolic sodium hydroxide (10 mL). To this stirred solution 3,4-methylenedioxybenzaldehyde (100 mg) was added and further stirred at room temperature at 30° C. for 1 hour. On completion, the reaction mixture was diluted with water, acidified with dil. HCl and extracted with ethyl acetate. The organic layer was washed with water, dried over anhydrous sodium sulphate and evaporated to get a residue. The residue was purified through silica gel column to get 2-benzo[1,3]dioxo-5-ylmethylene-4,5,6-trimethoxy-3-(3,4,5-trimethoxyphenyl)-indan-1-one (formula 8, 232 mg)

EXAMPLE 4

Step 1 to Step 5 Same as in Example 2

Step 6: Preparation of 2-(3,4-methylenedioxybenzylidine), 3-(3,4,5-trimethoxyphenyl), 4,5,6-trimethoxyindanone (Formula 8)

4,5,6-trimethoxy-3-(3,4,5-trimethoxyphenyl)-indan-1-one (formula 7, 250 mg) was taken in 5% aqueous-methanolic (1:3) potassium carbonate (10 mL). To this stirred solution 3,4-methylenedioxybenzaldehyde (100 mg) was added and further stirred at room temperature at 30° C. for 1 hour. On completion, the reaction mixture was diluted with water, acidified with dil. HCl and extracted with ethyl acetate. The organic layer was washed with water, dried over anhydrous sodium sulphate and evaporated to get a residue. The residue was purified through silica gel column to get 2-benzo[1,3]dioxo-5-ylmethylene-4,5,6-trimethoxy-3-(3,4,5-trimethoxyphenyl)-indan-1-one (formula 8, 206 mg)

A. In vitro Anticancer (Cytotoxicity) Activity Against Human Cancer Cell Lines The benzylidene analogues were evaluated by Sulphorhodamine B Assay as per reported method [Skehan et al., *J. Natl. Cancer Inst.* 1990, 82, 1107]. The human cancer cell lines procured from National Cancer institute, Frederick, U.S.A. were used in present study. Cells were grown in tissue culture flasks in complete growth medium (RPMI-1640 medium with 2 mM glutamine, pH 7.4 supplemented with 10% fetal bovine serum, 100 µg/ml streptomycin and 100 units/ml penicillin) in a carbon dioxide incubator (37° C., 5% $CO_2$ 90% RH). The cells at subconfluent stage were harvested from the flask by treatment with trypsin (0.05% in PBS (pH 7.4) containing 0.02% EDTA). Cells with viability of more than 98%, as determined by trypan blue exclusion, were used for determination of cytotoxicity. The cell suspension required concentration of cells was prepared in complete growth medium. Stock solution of $2 \times 10^{-2}$ M of compounds were prepared in DMSO and further dilution was carried out complete growth medium containing 50 µg/ml of gentamycin to obtained working test solution of required concentration. In vitro cytotoxicity against various human cancer cell lines was determined using 96-well cell culture plates. The 100 µl of cell suspension was added to each well of the 96-well cell culture plates. The cells were allowed to grow in $CO_2$ incubator (37° C., 5% $CO_2$, 90% RH) for 24 hours. The test materials in complete growth medium (100 µl) were added after 24 hours incubation to the wells containing cell suspension. The plates were further incubated for 48 hours (37° C. in an atmosphere of 5% $CO_2$ and 90% relative humidity) in a carbon dioxide incubator after addition of test material and then the cell growth was stopped by gently layering trichloroacetic acid (50% TCA, 50 µl) on top of the medium in all the wells. The plates were incubated at 4° C. for one hour to fix the cells attached to the bottom of the wells. The liquid of all the wells was gently pipetted out and discarded. The plates were washed five times with distilled water to remove TCA, growth medium low molecular weight metabolites, serum proteins etc. and air-dried. Cell growth was measured by staining with sulforhodamine B dye. The adsorbed dye was dissolved in Tris-HCl Buffer (100 µl/well, 0.01M, pH 10.4) and plates were gently stirred for 10 minutes on a mechanical stirrer. The optical density (OD) was recorded on ELISA reader at 540 nm. 5-Fluorouracil, Paclitaxel (Taxol), Mitomycin-c and Adriamycin were used as positive controls.

B. In-vitro Tubulin Polymerisation Inhibition Assay

The tubulin polymerization experiment was performed using 'assay kit' (Cytoskeleton USA) following manufacturer's protocol based on the procedure described by of Shelanski et al. (1973) and Lee et al. (1977). Briefly, tubulin protein (3 mg/mL) in tubulin polymerization buffer (80 mM PIPES, pH 6.9, 2 mM MgCl2, 0.5 mM EGTA, 1 mM GTP and 15% glycerol) was placed in pre-warmed 96-well microtiter plates at 37° C. in the presence of test compounds with variable concentrations. All samples were mixed well and polymerization was monitored kinetically at 340 nm every min for 1 h using a Spectramax plate reader. Podophyllotoxin and etoposide were used as positive controls and DMSO as negative control. The $IC_{50}$ value was determined from dose-dependent analysis and is defined as the concentration that inhibits the rate of polymerization by 50%.

Podophyllotoxin and etoposide, standard tubulin polymerisation inhibitors were used as positive controls.

TABLE 3

In-vitro anticancer (cytotoxicity) activity and tubulin polymerisation inhibition of benzylidene analogues.

| Compd. no. | Human cancer cell lines $IC_{50}$ (μM)* | | | | | | | Tubulin polymerisation inhibition $IC_{50}$ (μM)** |
|---|---|---|---|---|---|---|---|---|
| | A549 (Lung) | PC-3 (prostate) | HCT (Colon) | THP-1 (Leukemia) | HeLa (Cervix) | MCF-7 (Breast cancer) | DU-145 (prostate) | |
| 8 | 11 | Inactive | 0.1 | 4.9 | 23 | 0.01 | Inactive | 0.63 |
| 9 | 67.6 | Inactive | 39.7 | 64.9 | 82.3 | 38.9 | Inactive | 4.62 |
| 10 | 13.4 | 65.7 | 18.6 | 0.88 | 21 | 3.18 | 44.9 | 4.67 |
| 11 | Inactive | Inactive | 97.3 | 89.5 | Inactive | 88.1 | Inactive | Inactive |
| 12 | Inactive | Inactive | Inactive | Inactive | Inactive | Inactive | Inactive | Inactive |
| 13 | Inactive | Inactive | Inactive | 62 | Inactive | 80.8 | Inactive | 0.62 |
| 14 | 47.5 | 50.6 | 14.9 | 32.7 | 14.1 | 42.5 | Inactive | Inactive |
| 15 | 93 | 85 | 79.6 | Inactive | Inactive | 8.88 | Inactive | Inactive |
| 16 | 87.2 | 64.9 | Inactive | 81.5 | Inactive | 56.5 | Inactive | 4.21 |
| 17 | 82.2 | Inactive | 45.9 | Inactive | Inactive | 57.2 | Inactive | Inactive |
| 18 | 26.9 | 38.6 | Inactive | 2.88 | 66.5 | 0.68 | 54.1 | 0.73 |
| 19 | 62.6 | Inactive | Inactive | 29.3 | Inactive | — | 21.5 | Inactive |
| 20 | 61.5 | 27.9 | 92 | 8.67 | Inactive | 68.9 | Inactive | 0.60 |
| 21 | 71.6 | 71.7 | 11.1 | Inactive | Inactive | 1 | 2.04 | 3.04 |
| 22 | Inactive | 78.9 | Inactive | Inactive | Inactive | Inactive | 78.9 | Inactive |
| Podophyllotoxin | <1 | 91.5 | <1 | <1 | <1 | <1 | 91.5 | 0.31 |
| Etoposide | 5.4 | Inactive | 6.5 | <1 | <1 | 1.5 | Inactive | 0.33 |

| Positive controls | Concentration (μM) | % Inhibition | | | | | |
|---|---|---|---|---|---|---|---|
| | | HCT (Colon) | Hela (Cervix) | THP-1 (Leukemia) | A549 (Lung) | PC-3 (Prostate) | MCF-7 (Breast) |
| 5-Fluorouracil | 20 | 65 | 70 | 74 | — | — | — |
| Paclitaxel | 1 | — | — | — | 69 | — | — |
| Mitomycin-c | 1 | — | — | — | — | 61 | — |
| Adriamycin | 1 | — | — | — | — | — | 65 |

*inactive, if $IC_{50}$ > 100 μM;
**inactive, if $IC_{50}$ > 10 μM

In the present series of 2-benzylidene indanones (8-22) compounds showed potent anticancer activity mainly agsint Leukemia (THP-1) and breast cancer cell lines (MCF-7). Compounds 8, 10, 18 and 20 exhibited potent activity against leukemia cell lines (THP). While compounds 8, 10, 15, 18 and 21 have exhibited potent anticancer activity against human breast cancer cells. Thus, compounds 8, 10 and 18 were potent against both the cell lines. Compounds 8, 9, 10, 13, 16, 18, 20 and 21 showed strong inhibition of tubulin polymerase. Microtubules play an essential role in cell division. Tubulin polymerisation inhibitors inhibit mitosis or cell division. Such molecules prevent cancer cells to undergo mitosis by disrupting microtubule polymerisation and hence used in cancer treatment. In this series 8, 10, 18 and 21 are notable anticancer molecules and compound 8 is the best lead of the series.

C. In-vivo Acute Oral Toxicity in Swiss-albino Mice

In view of potent anti-cancer activity of compound 8 in in-vitro model, acute oral toxicity of the same was carried out in Swiss albino mice for its further development into drug product. For the study, 30 mice (15 male and 15 female) were taken and divided into five groups comprising 3 male and 3 female mice in each group weighing between 20-25 g. The animals were maintained at 22±5° C. with humidity control and also on an automatic dark and light cycle of 12 hours. The animals were fed with the standard rat feed and provided ad libitum drinking water. Mice of group 1 were kept as control and animals of groups 2, 3 and 4 were kept as experimental. The animals were acclimatized for 7 days in the experimental environment prior to the actual experimentation. The test compound was suspended by ultrasonication in cremophore EL (20% in distilled water) using traces of ethanol as a co-solvent and was given at 5, 50, 300 and 1000 mg/kg body weight to animals of groups 2, 3, 4 and 5 respectively. Control animals received only vehicle.

Observational, Haematological, Biochemical and Gross Pathological Study:

The animals were checked for mortality and any signs of ill health at hourly interval on the day of administration of drug and there after a daily general case side clinical examination was carried out including changes in skin, mucous membrane, eyes, occurrence of secretion and excretion and also responses like lachrymation, pilo-erection respiratory patterns etc. Also changes in gait. posture and response to handling were also recorded (Allan at al., 2007). In addition to observational study, body weights were recorded and blood and serum samples were collected from all the animals on 7th day after experiment and were analysed for total RBC, WBC, differential leucoyte count haemoglobin percentage and biochemical parameters like total cholesterol, triglycerides, creatinine, SGPT and SGOT activity. The animals were then sacrificed and were necropsed for any gross pathological changes. Weights of vital organs like liver, heart, kidney etc. were recorded (Chanda et al., 2009).

Table 4. Effect of compound 8 as a single acute oral dose at 5, 50, 300 and 1000 mg/kg body weight on body weight, haemogram and serum biochemical parameters in Swiss albino mice (Mean±SE; n=6; a, P<0.001 compared to control, 5, 50, 300 mg/kg).

Acute oral toxicity study of compound of formula 8 in Swiss albino mice

| Parameters | Control | 5 mg/kg | 50 mg/kg | 300 mg/kg | 1000 mg/kg |
| --- | --- | --- | --- | --- | --- |
| Dose of compound 8 at mg/kg body weight as a single oral dose | | | | | |
| Body weight (g) | 30.42 ± 1.25 | 30.38 ± 0.77 | 28.37 ± 1.42 | 29.35 ± 1.63 | 30.69 ± 0.83 |
| SGPT (U/L) | 9.30 ± 0.89 | 6.90 ± 0.17 | 9.77 ± 0.77 | 9.16 ± 1.14 | 19.68 ± 1.78[a] |
| SGOT (U/L) | 20.47 ± 2.07 | 18.74 ± 1.54 | 20.66 ± 1.15 | 26.55 ± 3.23 | 19.38 ± 3.49 |
| ALKP (U/L) | 83.29 ± 9.77 | 82.51 ± 3.04 | 94.24 ± 8.83 | 90.11 ± 5.42 | 171.12 ± 15.91[a] |
| Haemoglobin (g/dL) | 13.38 ± 1.00 | 11.31 ± 1.14 | 12.93 ± 0.98 | 11.46 ± 0.76 | 12.21 ± 1.46 |
| Serum total cholesterol (mg/dL) | 116.07 ± 8.86 | 109.42 ± 5.46 | 125.69 ± 5.90 | 117.57 ± 3.45 | 118.60 ± 6.07 |
| Serum triglycerides (mg/dL) | 101.29 ± 5.18 | 112.69 ± 3.75 | 90.62 ± 8.41 | 113.15 ± 3.65 | 97.44 ± 6.96 |
| Serum creatinine (mg/dL) | 0.47 ± 0.06 | 0.53 ± 0.04 | 0.45 ± 0.05 | 0.56 ± 0.07 | 0.42 ± 0.09 |

Figure 1B:
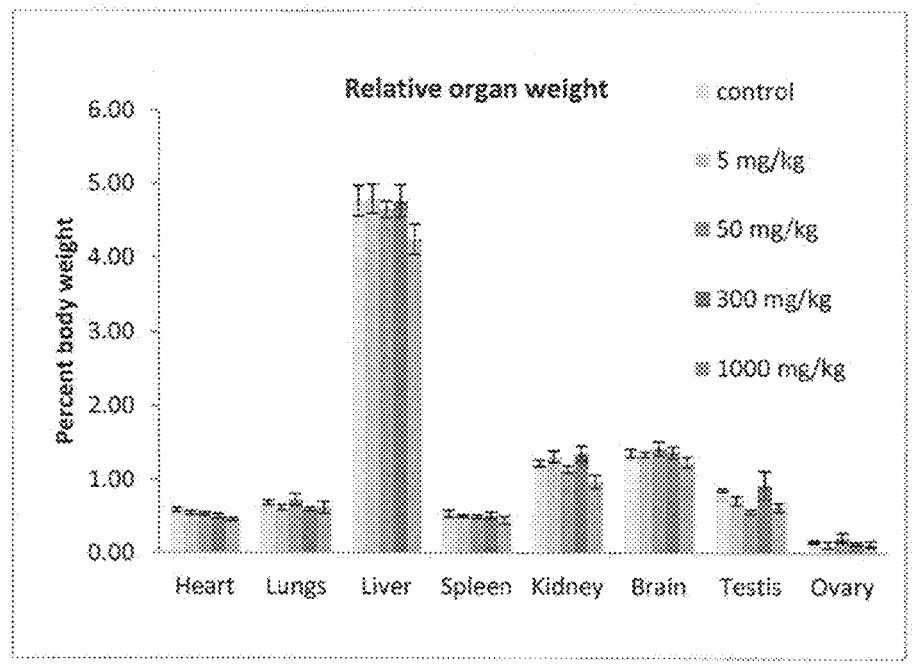
Figure 2:
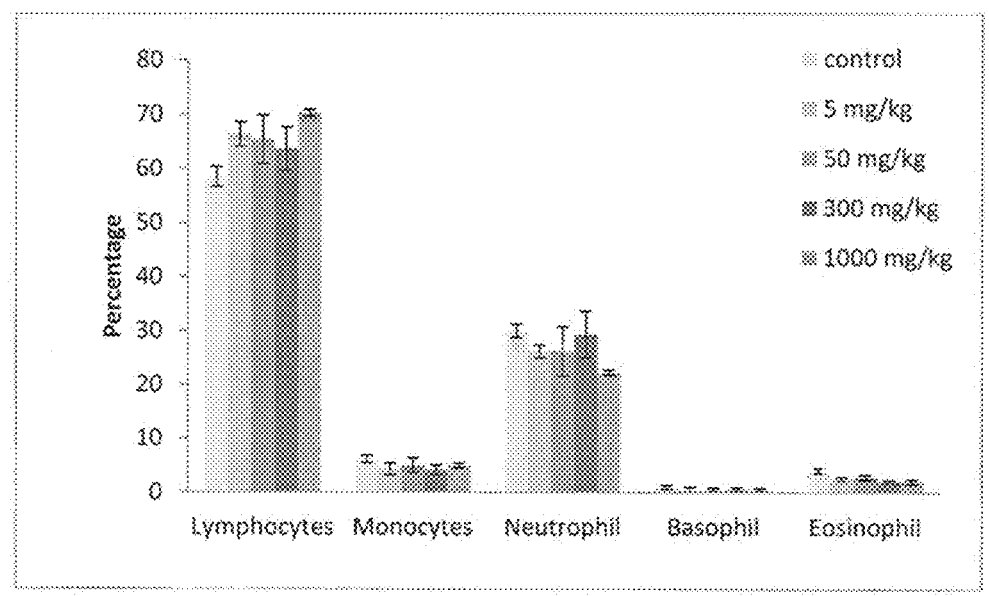
FIG. 2. Effect of compound 8 as a single acute oral dose at 5, 50, 300 and 1000 mg/kg body weight on differential leucocytes counts in Swiss albino mice. (n=6, Non significant changes were found compared to control).

No observational changes, morbidity and mortality were observed throughout the experimental period upto the dose level of 300 mg/kg body weight. However, two animals treated with compound 8 at 1000 mg/kg showed signs of excitement, hyperactivity for a very brief period of 10 min and was subsequently subsided. No morbidity or any other gross observation changes could be noticed in the group of animals treated with the test drug at 1000 mg/kg. Blood and serum samples upon analysis showed non-significant changes in all the parameters studied like total haemoglobin level, differential leucocyte count, serum total cholesterol, triglycerides, creatinine level and SGOT activity (Table 4 and FIG. 2). However, SGPT and ALKP activity showed significant increase in group of animals treated with the test drug at 1000 mg/kg. Animals on gross pathological study showed no changes in any of the organs studied including their absolute (FIG. 1A) and relative (FIG. 1B) weight. Therefore, it was found that compound 8 is well tolerated by the Swiss albino mice up to the dose level of 300 mg/kg body weight as a single acute oral dose.

Advantage: This is a novel series of compounds exhibiting anticancer (cytotoxic) activity and also tubulin polymerisation inhibition. This is also the first process of preparation of these compounds.

We claim:

1. A compound of formula (I),

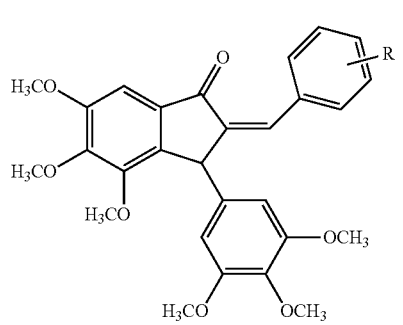

(I)

wherein R is selected from the group consisting of H, 3,4-methylenedioxy, 3,4,5-trimethoxy, 4-methoxy, 4-nitro, 3-nitro, 3,4-dimethoxy, 2,3,4-trimethoxy, 2,4,5-trimethoxy, 2,3-methylenedioxy, 4-fluoro, 2-methoxy, 4-trifluoromethyl, 2,4-dimethoxy and 4-benzyloxy.

2. A compound as claimed in claim 1, wherein the structural formula of the compound is one of the following structural formulae:

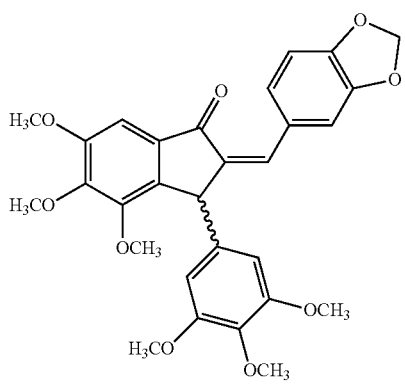

8

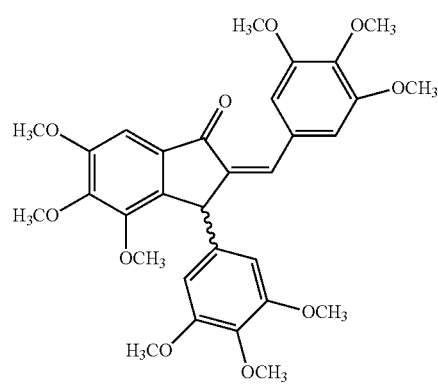

9

10
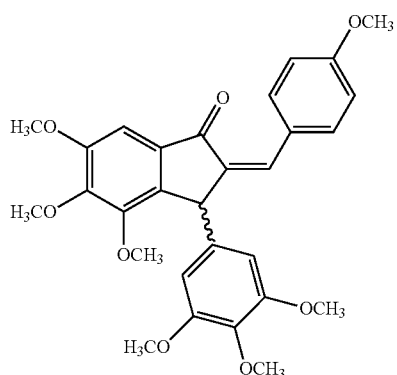
11
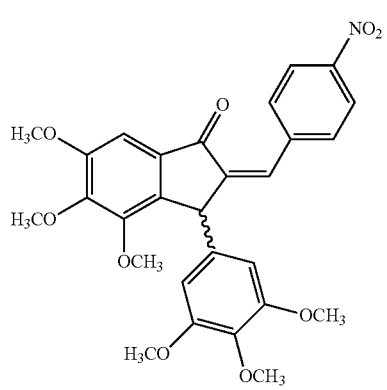
12
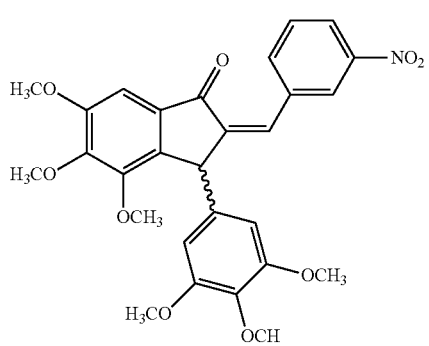
13
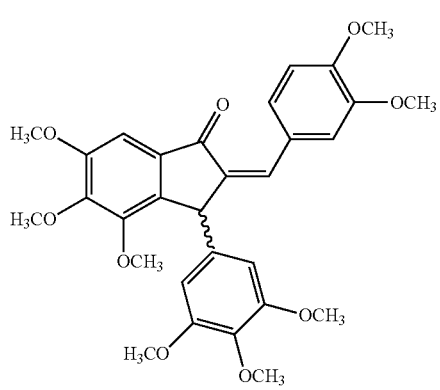
14
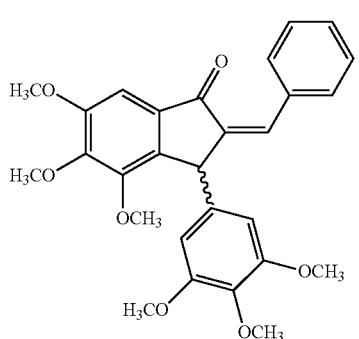
15
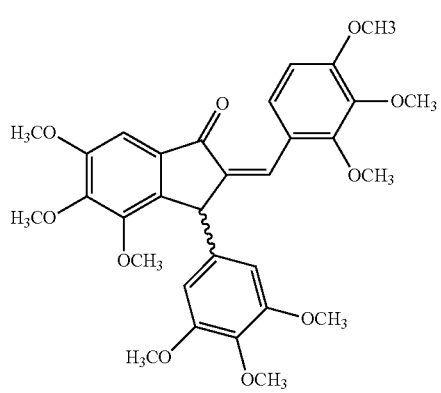
16
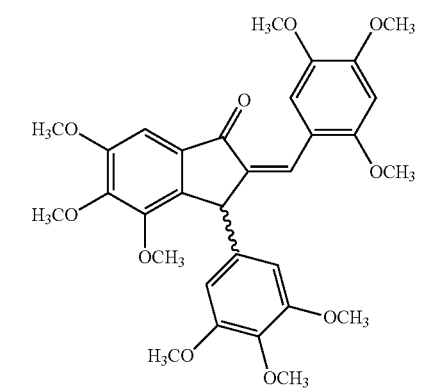
17
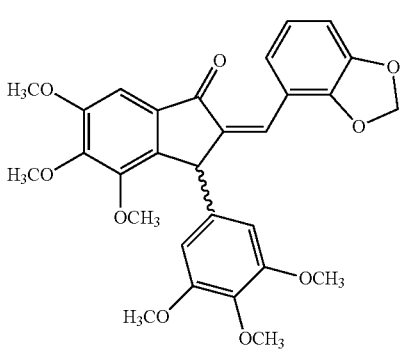

18

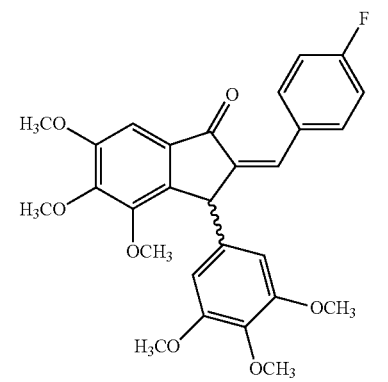

19

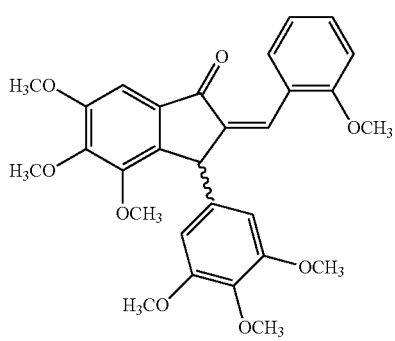

20

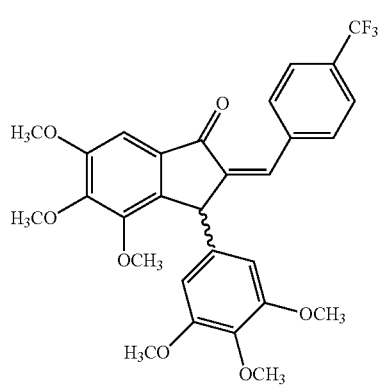

21

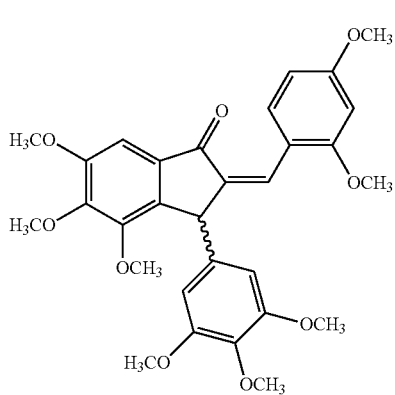

22

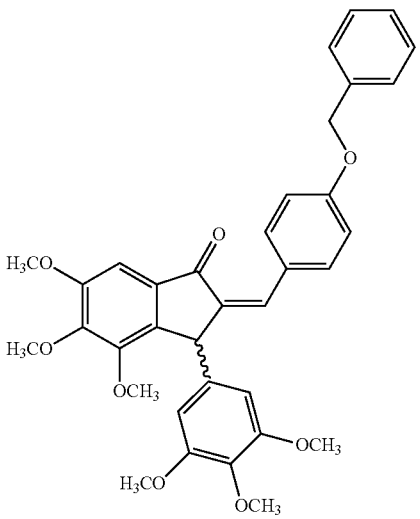

3. The compound as claimed in claim 1 which is 2-(3,4-methylenedioxybenzylidine), 3-(3,4,5-trimethoxyphenyl), 4,5,6-trimethoxyindanone.

4. A process for preparing a compound as claimed in claim 1, wherein the process comprises the steps:

(a) reacting 4,5,6-trimethoxy-3-(3,4,5-trimethoxyphenyl)-indan-1-one with an aromatic aldehyde in alkaline solution in aqueous alcohol at a temperature ranging between 20 to 35° C. to for a period ranging between 1 hour and 4 hours, wherein the aldehyde is selected from the group consisting of 3,4-methylenedioxybenzaldehyde; 3,4,5-trimethoxybenzaldehyde; 4-methoxybenzaldehyde; 4-nitrobenzaldehyde; 3-nitrobenzaldehyde; 3,4,-dimethoxybenzaldehyde; benzaldehyde; 2,3,4-trimethoxybenzaldehyde; 2,4,5-trimethoxybenzaldehyde; 2,3-methylenedioxybenzaldehyde; 4-fluorobenzaldehyde; 2-methoxybenzaldehyde; 4-trifluoromethylbenzaldehyde; 2,4,-dimethoxybenzaldehyde; and 4-benzyloxybenzaldehyde, (b) diluting the reaction mixture from step (a) with water and acidifying the mixture with HCl followed by extraction with a water immiscible solvent and evaporation to obtain a residue, and (c) purifying the residue of step (b) by chromatographic methods to give a compound of claim 1.

5. The process as claimed in claim 4 wherein the alkali in the alkaline solution is selected from the group consisting of potassium hydroxide, sodium hydroxide, lithium hydroxide, potassium carbonate and sodium carbonate.

6. The process as claimed in claim 4 wherein the alkaline solution ranges between 3% to 10%.

7. The process as claimed in claim 4 wherein the alcohol comprising the aqueous alcohol is selected from the group consisting of methanol and ethanol, wherein the alcoholic concentration in the aqueous alcohol ranges between 50% to 100% in water.

8. A composition comprising:
a compound of formula (I):

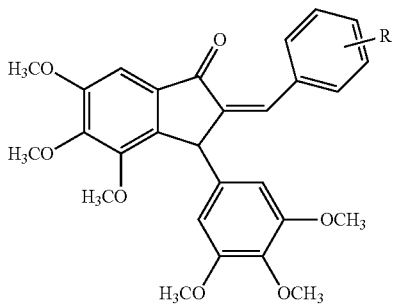

wherein R is selected from the group consisting of H, 3,4-methylenedioxy, 3,4,5-trimethoxy, 4-methoxy, 4-nitro, 3-nitro, 3,4-dimethoxy, 2,3,4-trimethoxy, 2,4,5-trimethoxy, 2,3-methylenedioxy, 4-fluoro, 2-methoxy, 4-trifluoromethyl, 2,4-dimethoxy and 4-benzyloxy; and a pharmaceutically acceptable excipient.

9. A method of treating a cancer selected from the group consisting of lung cancer, prostate cancer, colon cancer, cervical cancer, breast cancer and leukemia comprising administering to a patient in need thereof a therapeutically effective amount of one or more compounds of formula (1):

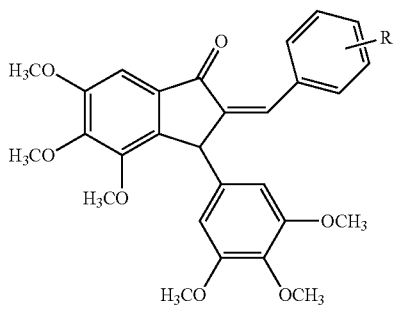

wherein R is selected from the group consisting of H, 3,4-methylenedioxy, 3,4,5-trimethoxy, 4-methoxy, 4-nitro, 3-nitro, 3,4-dimethoxy, 2,3,4-trimethoxy, 2,4,5-trimethoxy, 2,3-methylenedioxy, 4-fluoro, 2-methoxy, 4-trifluoromethyl, 2,4-dimethoxy and 4-benzyloxy.

* * * * *